(12) United States Patent
Patil et al.

(10) Patent No.: US 11,903,768 B2
(45) Date of Patent: Feb. 20, 2024

(54) METHOD AND SYSTEM FOR PROVIDING ULTRASOUND IMAGE ENHANCEMENT BY AUTOMATICALLY ADJUSTING BEAMFORMER PARAMETERS BASED ON ULTRASOUND IMAGE ANALYSIS

(71) Applicant: GE Precision Healthcare LLC, Wauwatosa, WI (US)

(72) Inventors: Abhijit Patil, Maharashtra (IN); Vikram Melapudi, Karnataka (IN); Krishna Seetharam Shriram, Karnataka (IN); Chandan Kumar Mallappa Aladahalli, Karnataka (IN)

(73) Assignee: GE Precision Healthcare LLC, Waukesha, WI (US)

( * ) Notice: Subject to any disclaimer, the term of this patent is extended or adjusted under 35 U.S.C. 154(b) by 855 days.

(21) Appl. No.: 16/673,644

(22) Filed: Nov. 4, 2019

(65) Prior Publication Data
US 2021/0128114 A1   May 6, 2021

(51) Int. Cl.
*A61B 8/08* (2006.01)
*G02B 27/09* (2006.01)
(Continued)

(52) U.S. Cl.
CPC .......... *A61B 8/483* (2013.01); *A61B 6/5258* (2013.01); *G02B 27/0916* (2013.01); *G06T 7/0012* (2013.01); *G06T 2207/10132* (2013.01)

(58) Field of Classification Search
CPC ......... A61B 8/483; A61B 6/5258; A61B 8/54; A61B 8/5269; A61B 8/08; A61B 8/52;
(Continued)

(56) References Cited

U.S. PATENT DOCUMENTS 8,761,469 B2   6/2014 Kemp
2016/0143617 A1*  5/2016 Ebbini ................ G01S 15/8915
600/447

(Continued)

OTHER PUBLICATIONS

Bell et al., Ultrasound artifacts, website link: https://radiopaedia. org/articles/ultrasound-artifacts-3, Jul. 11, 2019, see wayback machine attachment.*

(Continued)

*Primary Examiner* — Bo Joseph Peng
(74) *Attorney, Agent, or Firm* — McAndrews, Held & Malloy, Ltd.; Daniel Bissing; David Bates (57) ABSTRACT

A system and method for automatically adjusting beamformer parameters based on ultrasound image analysis to enhance ultrasound image acquisition is provided. The method includes acquiring, by an ultrasound system, an ultrasound image. The method includes segmenting, by at least one processor, the ultrasound image to identify anatomical structure(s) and/or image artifact(s) in the ultrasound image. The method includes detecting, by the at least one processor, a location of each of the identified anatomical structure(s) and/or image artifact(s). The method includes automatically adjusting, by the at least one processor, at least one beamformer parameter based on the detected location of one or more of the identified anatomical structure(s) and/or the image artifact(s). The method includes acquiring, by the ultrasound system, an enhanced ultrasound image based on the automatically adjusted at least one beamformer parameter. The method includes presenting, at a display system, the enhanced ultrasound image.

20 Claims, 4 Drawing Sheets (51) Int. Cl.
*A61B 6/00* (2006.01)
*G06T 7/00* (2017.01)

(58) Field of Classification Search
CPC .............. G02B 27/0916; G06T 7/0012; G06T 2207/10132; G06T 2207/20081; G06T 2207/20084; G06T 2207/20092; G06T 7/11

See application file for complete search history.

(56) References Cited

U.S. PATENT DOCUMENTS

2018/0085096 A1  3/2018  Brandl
2018/0160981 A1  6/2018  Tsymbalenko et al.
2018/0275258 A1  9/2018  Pintoffl et al.

OTHER PUBLICATIONS

Ilovitsch, et al., "Imaging beyond ultrasonically-impenetrable objects," Scientific Reports 8, Article No. 5759 (2018), Apr. 10, 2018, pp. 1-11.

* cited by examiner

METHOD AND SYSTEM FOR PROVIDING ULTRASOUND IMAGE ENHANCEMENT BY AUTOMATICALLY ADJUSTING BEAMFORMER PARAMETERS BASED ON ULTRASOUND IMAGE ANALYSIS

FIELD

Certain embodiments relate to ultrasound imaging. More specifically, certain embodiments relate to a method and system for automatically adjusting beamformer parameters based on ultrasound image analysis to enhance ultrasound image acquisition.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

Ultrasound is a key modality to make healthcare accessible due to its affordability, non-invasive nature, and compact form factor. Ultrasound array probes have played a vital role in obtaining clinically relevant images having clarity and resolution in a short time. Typically, the excitation and receiver settings of an ultrasound probe are either fixed or offer minimal user control due to the intricate knowledge of the hardware and the image generation process from raw signals needed to manually modify the settings. Accordingly, a clinician may move the probe to attempt to find a desired anatomical view instead of altering acquisition settings, such as transmitter and receiver patterns. However, the clinician may settle for sub-optimal images for certain anatomies that may be difficult to image or due to time constraints.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically adjusting beamformer parameters based on ultrasound image analysis to enhance ultrasound image acquisition, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for automatically adjusting beamformer parameters based on ultrasound image analysis to enhance ultrasound image acquisition. Various embodiments have the technical effect of dynamically identifying anatomical structures and artifacts in ultrasound images. Aspects of the present disclosure have the technical effect of dynamically identifying obstructing anatomies and regions for improved insonation. Certain embodiments have the technical effect of enhancing ultrasound image acquisition by dynamically adjusting ultrasound beamformer parameters based on the identification of obstructing anatomies and regions for improved insonation.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
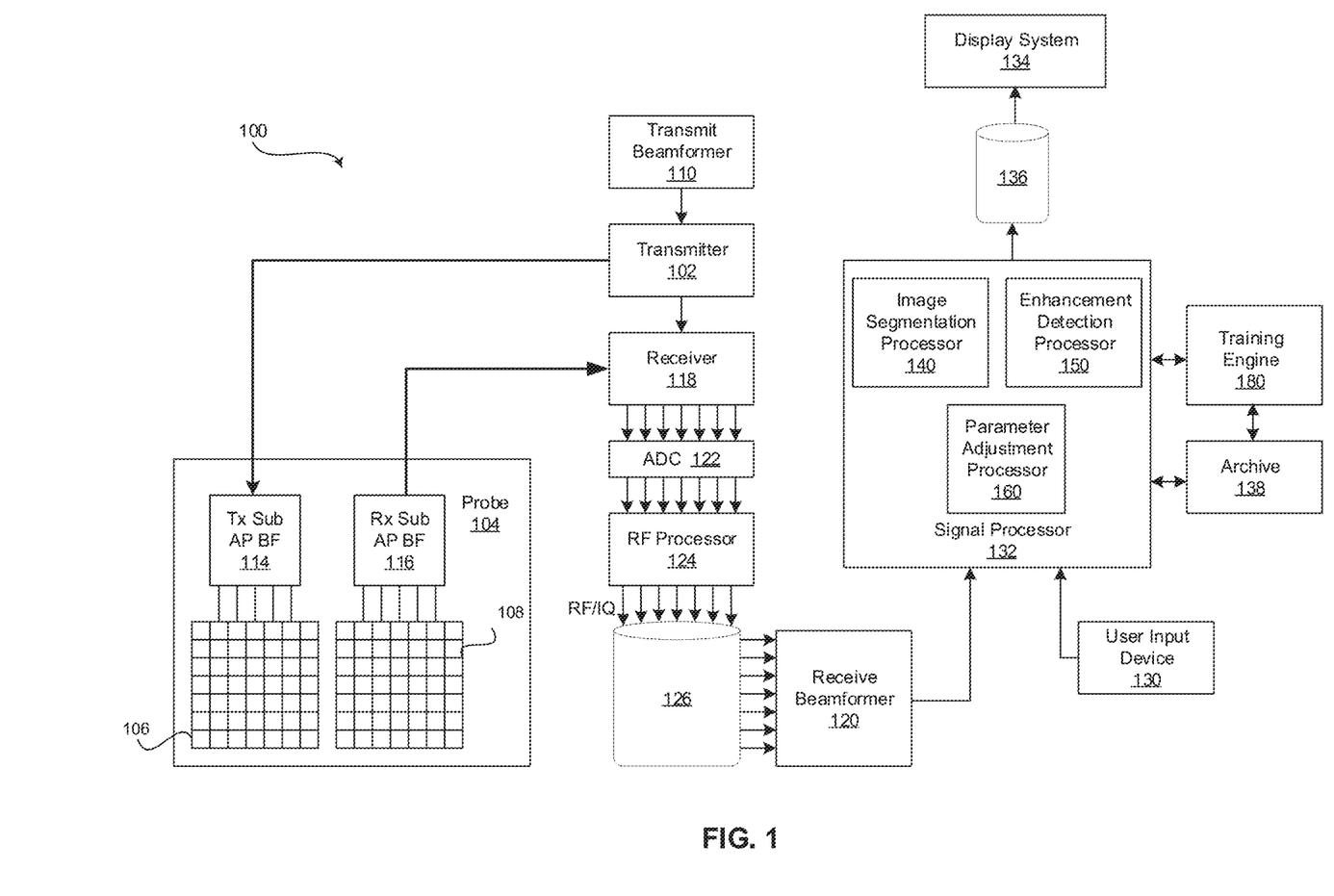
FIG. 1 is a block diagram of an exemplary ultrasound system that is operable to provide ultrasound image enhancement by automatically adjusting beamformer parameters based on ultrasound image analysis, in accordance with various embodiments.

FIG. 1 is a block diagram of an exemplary ultrasound system 100 that is operable to provide ultrasound image enhancement by automatically adjusting beamformer parameters based on ultrasound image analysis, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, an archive 138, and a training engine 180.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise an image segmentation processor 140, an enhancement detection processor 150, and a parameter adjustment processor 160. The signal processor 132 may be capable of receiving input information from a user input device 130 and/or archive 138, generating an output displayable by a display system 134, and manipulating the output in response to input information from a user input device 130, among other things. The signal processor 132, image segmentation processor 140, enhancement detection processor 150, and parameter adjustment processor 160 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an image segmentation processor 140 that comprises suitable logic, circuitry, interfaces and/or code that may be operable to analyze acquired ultrasound images to identify and segment anatomical structures and image artifacts, such as a liver, gall bladder, bowel, diaphragm, kidney, rib or other shadows, dark regions at posterior region of kidney cyst, lack of twinkling at calcification-like mass in a gall bladder, or any suitable anatomical structures or image artifact. The image segmentation processor 140 may include artificial intelligence image analysis algorithms, one or more deep neural networks (e.g., a convolutional neural network) and/or may utilize any suitable form of artificial intelligence image analysis techniques or machine learning processing functionality configured to analyze acquired ultrasound images to identify and segment anatomical structures and image artifacts.

The image segmentation processor 140 may comprise suitable logic, circuitry, interfaces and/or code that may be operable to analyze acquired ultrasound images to identify and segment anatomical structures and image artifacts. In various embodiments, the image segmentation processor 140 may be provided as a deep neural network that may be made up of, for example, an input layer, an output layer, and one or more hidden layers in between the input and output layers. Each of the layers may be made up of a plurality of processing nodes that may be referred to as neurons. For example, the image segmentation processor 140 may include an input layer having a neuron for each pixel or a group of pixels from a scan plane of an anatomical structure. The output layer may have a neuron corresponding to a plurality of pre-defined anatomical structures. As an example, if performing an ultrasound procedure of the heart, the output layer may include neurons for a mitral valve, aortic valve, ventricle chambers, atria chambers, septum, papillary muscle, inferior wall, rib shadow artifacts, and the like. Other ultrasound procedures may utilize output layers that include neurons for a liver, gall bladder, bowel, diaphragm, nerves, vessels, bones, shadow artifacts, dark region artifacts, or any suitable anatomical structure and/or image artifact. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the image segmentation processor 140 deep neural network (e.g., convolutional neural network) may identify anatomical structures and image artifacts in ultrasound image data with a high degree of probability.

In certain embodiments, the image segmentation processor 140 may be configured to identify and segment anatomical structures and image artifacts based on a user instruction via the user input device 130. For example, the image segmentation processor 140 may be configured to interact with a user via the user input device 130 to receive instructions for searching the ultrasound image. As an example, a user may provide a voice command, probe gesture, button depression, or the like that instructs the image segmentation processor 140 to search for a particular structure or artifact and/or to search a particular region of the ultrasound image.

Figure 2:
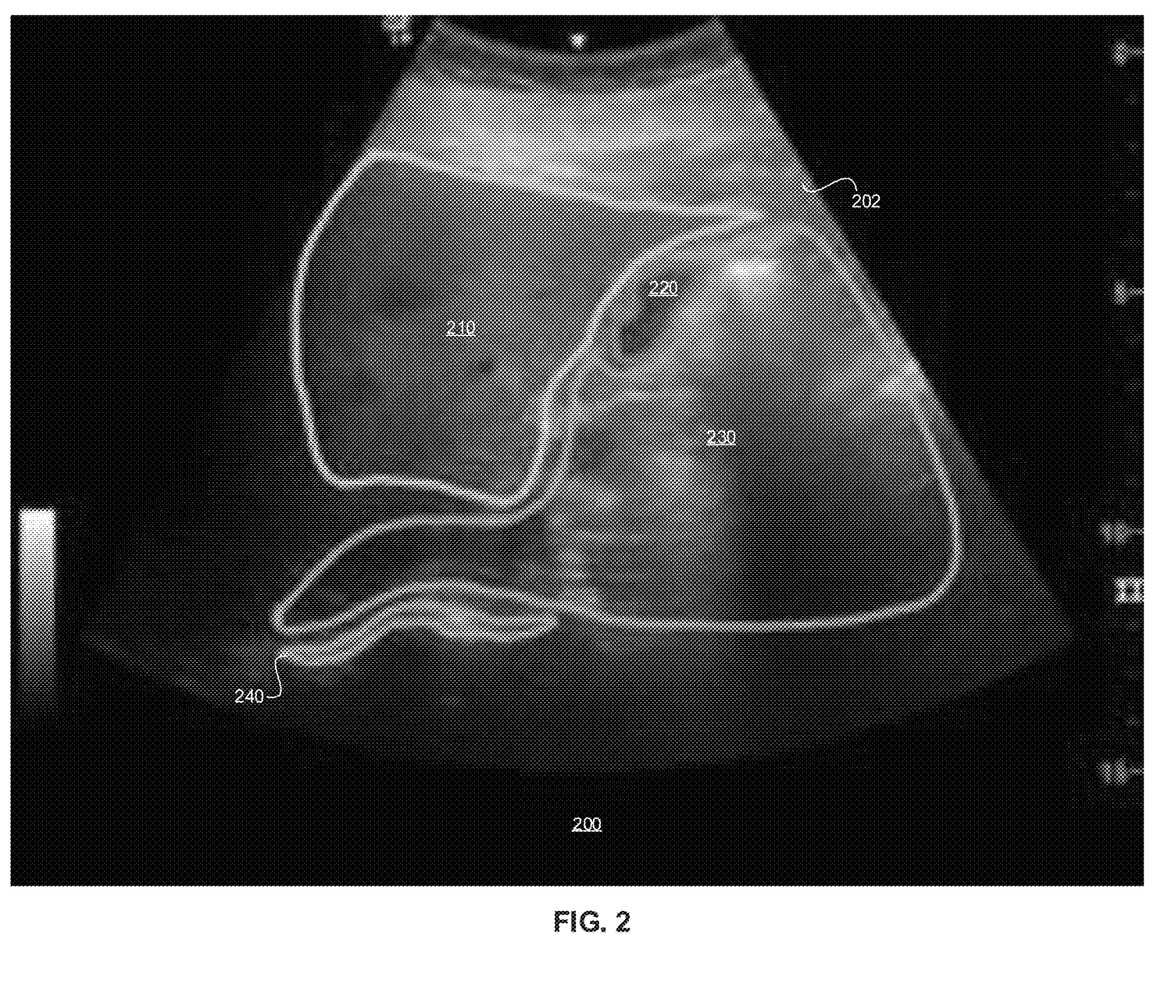
FIG. 2 is a display of an exemplary ultrasound image identifying anatomical structures, in accordance with various embodiments.

FIG. 2 is a display 200 of an exemplary ultrasound image 202 identifying anatomical structures 210-240, in accordance with various embodiments. Referring to FIG. 2, the ultrasound image 202 may comprise structures 210, 220, 230, 240 identified and segmented by the image segmentation processor 140. For example, the structures may comprise a liver 210, a gall bladder 220, a bowel 230, and a diaphragm 240.

Referring again to FIG. 1, the signal processor 132 may include an enhancement detection processor 150 that comprises suitable logic, circuitry, interfaces and/or code that may be operable to determine whether and where to perform image enhancement based on the anatomical structures and image artifacts identified by the image segmentation processor 140. For example, the enhancement detection processor 150 may determine not to perform image enhancement if the image segmentation processor 140 does not identify any image artifacts and/or if anatomical structures associated with known or detected imaging deficiencies are not present in the ultrasound image as identified by the image segmentation processor 140. As another example, the enhancement detection processor 150 may determine to perform image enhancement and identify locations in the ultrasound image for enhancement based on the locations of image artifacts identified by the image segmentation processor 140 and locations of obstructing anatomical structures identified by the image segmentation processor 140 that may be associated with the image artifacts. Additionally, the enhancement detection processor 150 may determine to perform enhancement based on the presence of particular anatomical structures identified by the image segmentation processor 140 that have known or detected imaging deficiencies. More specifically, certain anatomies, such as a gall bladder or any suitable anatomical structure, may be known to be acoustically hard such that the anatomical structure obscures regions directly below the structure with hard or soft shadows. The enhancement detection processor 150 may detect the location of the shadows and the location of the obstructing anatomical structure to provide to the parameter adjustment processor 160 to enhance the ultrasound image. As another example, the enhancement detection processor 150 may detect a location of an anatomy of interest as defined by a protocol or user input to provide to the parameter adjustment processor 160 to enhance the ultrasound image. Additionally, the enhancement detection processor 150 may detect the location of an anatomical structure having a known or detected imaging deficiency, such as a twinkling effect that may appear when imaging a gall bladder, and may provide the location of the anatomical structure having the known or detected imaging deficiency to the parameter adjustment processor 160 to enhance the ultrasound image.

Figure 3:
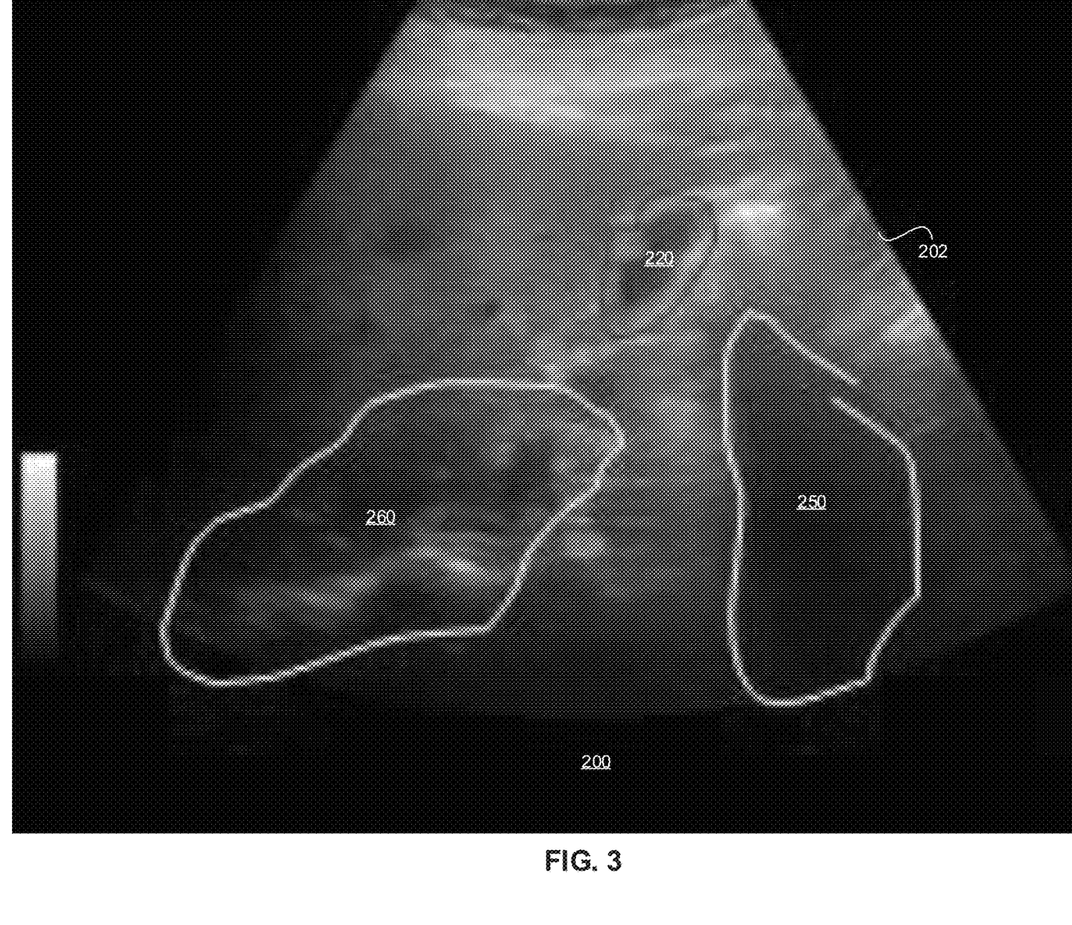
FIG. 3 is a display of an exemplary ultrasound image identifying an obstacle and image regions for enhancement, in accordance with various embodiments.

FIG. 3 is a display 200 of an exemplary ultrasound image 202 identifying an obstacle 220 and image regions 250, 260 for enhancement, in accordance with various embodiments. Referring to FIG. 3, the ultrasound image 202 may comprise locations of obstacles 220 and image artifacts 250, 260 detected by the enhancement detection processor 150 based on the anatomical structures and image artifacts identified and segmented by the image segmentation processor 140. For example, the obstacle 220 may be a gall bladder 220 and the image artifacts 250, 260 may include shadows 250 and dark regions 260. The locations of the obstacles 220 and image artifacts 250, 260 may be provided to the parameter adjustment processor 160.

Referring again to FIG. 1, the signal processor 132 may include a parameter adjustment processor 160 that comprises suitable logic, circuitry, interfaces and/or code that may be operable to adjust beamformer parameters in response to the locations of anatomical structures, obstacles, and/or image artifacts provided by the enhancement detection processor 150 to acquire enhanced ultrasound images having improved insonation of a particular region or regions. Beamformer parameters, as referred to herein, include both transmit and receive beamforming parameters, such as a number and position of activated and deactivated transducer elements, transducer element weights, delays, beam angles, and the like. In various embodiments, the parameter adjustment processor 160 may be operable to adjust the beamformer parameters to go around or otherwise avoid acoustically hard anatomies detected by the enhancement detection processor 150 to enhance regions below the acoustically hard anatomies by eliminating shadows and dark regions. For example, the parameter adjustment processor 160 may deactivate transducer elements adjacent ribs to avoid rib shadows and/or may adjust beamforming weights and/or beam angles to capture image data below the ribs, a gall bladder, or other acoustically hard anatomy as detected by the enhancement detection processor 150. In certain embodiments, the parameter adjustment processor 160 may be operable to adjust the beamformer parameters to improve image contrast and/or sharpness of an anatomy of interest detected by the enhancement detection processor 150. In an exemplary embodiment, the parameter adjustment processor 160 may be operable to adjust beamformer parameters to avoid image artifacts detected by the enhancement detection processor 150, such as haze or a twinkling effect of the gall bladder, among other things. For example, in a gall bladder stone ultrasound procedure, the parameter adjustment processor 160 may reduce a pulse repetition frequency and change a focal zone to just below a calcification in a gall bladder if the calcification-like mass includes twinkling artifacts as detected by the enhancement detection processor 150. As another example, in a kidney cyst ultrasound examination, the parameter adjustment processor 160 may turn on harmonics to improve insonation of a posterior of a cyst if the posterior region of the cyst includes a dark region image artifact detected by the enhancement detection processor 150. The ultrasound system 100 may be operable to acquire a next ultrasound image based on the beamformer parameters adjusted by the parameter adjustment processor 160 to present the enhanced ultrasound image at the display system 134.

Still referring to FIG. 1, the display system 134 may be any device capable of communicating visual information to a user. For example, a display system 134 may include a liquid crystal display, a light emitting diode display, and/or any suitable display or displays. The display system 134 can be operable to present ultrasound images and/or any suitable information. For example, the enhanced ultrasound images acquired with the adjusted beamformer parameters may be presented at the display system 134.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound image data, identification instructions, segmentation instructions, enhancement instructions, and parameter adjustment instructions, for example.

The training engine 180 may comprise suitable logic, circuitry, interfaces and/or code that may be operable to train the neurons of the deep neural network(s) of the image segmentation processor 140. For example, the artificial image segmentation processor 140 may be trained to automatically identify and segment anatomical structures and image artifacts provided in an ultrasound scan plane. For example, the training engine 180 may train the deep neural networks of the image segmentation processor 140 using databases(s) of classified ultrasound images of various anatomical structures and image artifacts. As an example, the image segmentation processor 140 may be trained by the training engine 180 with ultrasound images of particular anatomical structures and image artifacts to train the image segmentation processor 140 with respect to the characteristics of the particular structure or artifact, such as the appearance of structure edges, the appearance of structure shapes based on the edges, the positions of the shapes relative to landmarks in the ultrasound image data, and the like. In an exemplary embodiment, the structures may include a heart, liver, gall bladder, bowel, diaphragm, nerves, vessels, bones, shadow artifacts, dark region artifacts, and/or any suitable anatomical structure and/or image artifact. The anatomical structure and/or image artifact information may include information regarding the edges, shapes, and positions of the liver, gall bladder, bowel, diaphragm, nerves, vessels, bones, shadow artifacts, dark region artifacts, or any suitable anatomical structure and/or image artifact. In various embodiments, the databases of training images may be stored in the archive 138 or any suitable data storage medium. In certain embodiments, the training engine 180 and/or training image databases may be external system(s) communicatively coupled via a wired or wireless connection to the ultrasound system 100.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Figure 4:
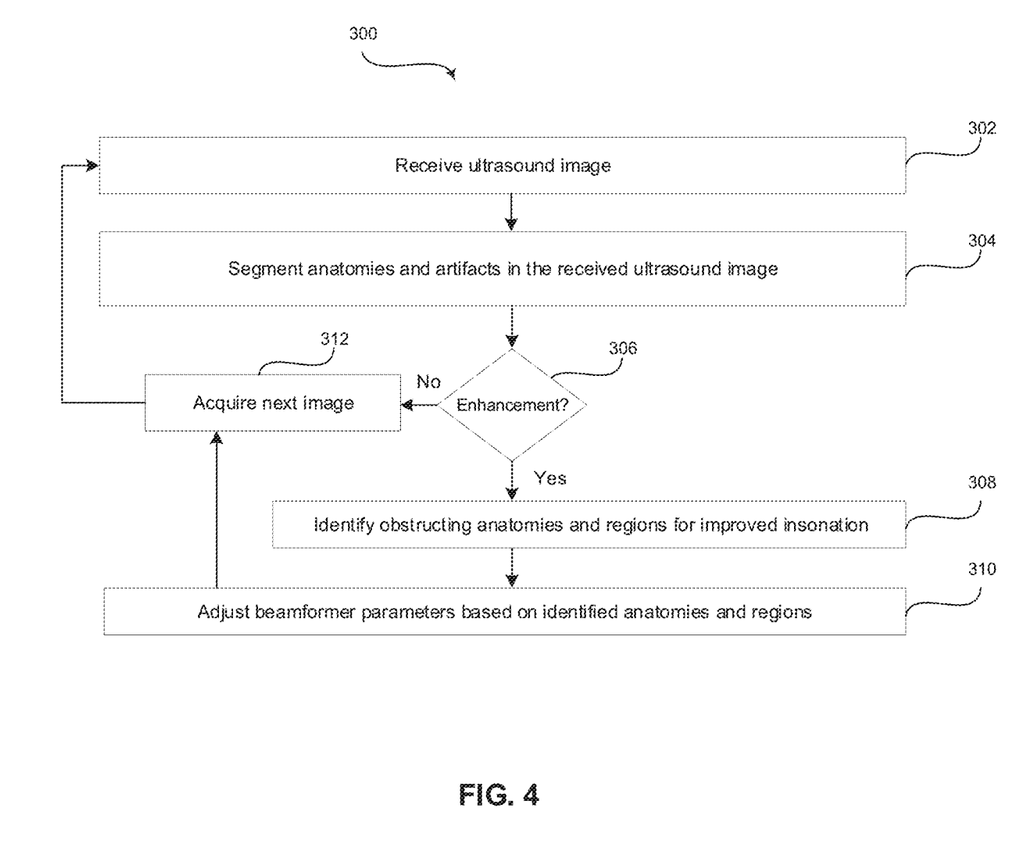
FIG. 4 is a flow chart illustrating exemplary steps that may be utilized for providing ultrasound image enhancement by automatically adjusting beamformer parameters based on ultrasound image analysis, in accordance with various embodiments.

FIG. 4 is a flow chart 300 illustrating exemplary steps 302-312 that may be utilized for providing ultrasound image enhancement by automatically adjusting beamformer parameters based on ultrasound image analysis, in accordance with various embodiments. Referring to FIG. 4, there is shown a flow chart 300 comprising exemplary steps 302 through 312. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, a signal processor 132 of an ultrasound system 100 receives an ultrasound image 202. For example, the ultrasound system 100 may acquire an ultrasound image 202 with an ultrasound probe 104 positioned at a scan position over region of interest. The ultrasound image may be provided to the signal processor 132 for processing and presentation at a display system 134 of the ultrasound system 100. The ultrasound system may acquire the image according to a protocol corresponding with a desired imaging procedure, such as a gall bladder stone procedure, a kidney cyst procedure, or any suitable procedure.

At step 304, a signal processor 132 of the ultrasound system 100 segments anatomical structures 210-240 and/or image artifacts 250, 260 in the received ultrasound image 202. For example, an image segmentation processor 140 of the signal processor 132 may be configured to analyze the ultrasound image 202 acquired at step 302 to identify and segment anatomical structures 210-240 and/or image artifacts 250, 260. The image segmentation processor 140 may include artificial intelligence image analysis algorithms, one or more deep neural networks (e.g., a convolutional neural network) and/or may utilize any suitable form of artificial intelligence image analysis techniques or machine learning processing functionality configured to analyze acquired ultrasound images to identify and segment anatomical structures 210-240 and/or image artifacts 250, 260 in the ultrasound image 202.

At step 306, the signal processor 132 of the ultrasound system 100 may determine whether to perform image enhancement. For example, an enhancement detection processor 150 of the signal processor 132 may analyze any anatomical structures 210-240 and image artifacts 250, 260 segmented by the image segmentation processor 140 at step 304. The enhancement detection processor 150 may determine not to perform image enhancement if the image segmentation processor 140 does not identify any image artifacts 250, 260 and/or if anatomical structures 210-240 associated with known or detected imaging deficiencies are not present in the ultrasound image as identified by the image segmentation processor 140. The process 300 may proceed to step 312 to acquire a next ultrasound image 202 if the enhancement detection processor 150 determines not to perform enhancement. As another example, the enhancement detection processor 150 may determine to perform image enhancement based on the presence of image artifacts 250, 260 identified by the image segmentation processor 140, the presence of obstructing anatomical structures 220 identified by the image segmentation processor 140 that may be associated with the image artifacts 250, 260, and/or the presence of particular anatomical structures 210-240 identified by the image segmentation processor 140 that have known or detected imaging deficiencies. The process 300 may proceed to step 308 if the enhancement detection processor 150 determines to perform image enhancement.

At step 308, the signal processor 132 of the ultrasound system 100 may identify obstructing anatomical structures 220 and/or regions for improved insonation 250, 260. For example, the enhancement detection processor 150 of the signal processor 132 may be configured to identify locations in the ultrasound image 202 for enhancement based on the locations of image artifacts 250, 260 identified by the image segmentation processor 140, locations of obstructing anatomical structures 220 identified by the image segmentation processor 140 that may be associated with the image artifacts 250, 260. and/or the locations of any anatomical structures identified by the image segmentation processor 140 that have known or detected imaging deficiencies. The locations of any image artifacts 250, 260, obstructing anatomical structures 220, and/or deficient anatomical structures may be provided by the enhancement detection processor 150 to a parameter adjustment processor 160 of the signal processor 132.

At step 310, the signal processor 132 of the ultrasound system 100 may adjust beamformer parameters based on identified anatomies and regions. For example, the parameter adjustment processor 160 of the signal processor 132 may receive the locations of any image artifacts 250, 260, obstructing anatomical structures 220, and/or deficient anatomical structures from the enhancement detection processor 150. The parameter adjustment processor 160 may be operable to adjust the transmit and receive beamforming parameters, such as a number and position of activated and deactivated transducer elements, transducer element weights, delays, beam angles, and the like, based on the received locations. For example, the parameter adjustment processor 160 may be operable to adjust the beamformer parameters to go around or otherwise avoid locations having acoustically hard anatomies by deactivating select transducer elements, adjusting beamforming weights, and/or adjusting beam angles to capture image data below the acoustically hard anatomy. As another example, the parameter adjustment processor 160 may be operable to adjust the beamformer parameters to improve image contrast and/or sharpness at a location of an anatomy of interest. Additionally and/or alternatively, the parameter adjustment processor 160 may be operable to adjust beamformer parameters to avoid image artifacts by changing a pulse repetition frequency, focal zone, and/or turning on harmonics, among other things.

At step 312, the ultrasound system 100 may acquire a next ultrasound image 202. For example, the ultrasound system 100 may be operable to acquire a next ultrasound image based on the beamformer parameters adjusted by the parameter adjustment processor 160. The ultrasound system 100 may acquire the ultrasound image 202 with an ultrasound probe 104 positioned at a scan position over region of interest. The process 300 may then return to step 302 to process and present the enhanced ultrasound image at the display system 134 of the ultrasound system 100.

Aspects of the present disclosure provide a method 300 and system 100 for providing ultrasound image enhancement by automatically adjusting beamformer parameters based on ultrasound image analysis. In accordance with various embodiments, the method 300 may comprise acquiring 302, by an ultrasound system 100, an ultrasound image 202. The method 300 may comprise segmenting 304, by at least one processor 132, 140, the ultrasound image 202 to identify at least one anatomical structure 210-240 and/or at least one image artifact 250, 260 in the ultrasound image 202. The method 300 may comprise detecting 308, by the at least one processor 132, 150, a location of each of the identified at least one anatomical structure 210-240 and/or the at least one image artifact 250, 260. The method 300 may comprise automatically adjusting 310, by the at least one processor 132, 160, at least one beamformer parameter based on the detected location of one or more of the identified at least one anatomical structure 210-240 and/or the at least one image artifact 250, 260. The method 300 may comprise acquiring 312, by the ultrasound system 100, an enhanced ultrasound image 202 based on the automatically adjusted at least one beamformer parameter. The method 300 may comprise presenting 302, at a display system 134, the enhanced ultrasound image.

In an exemplary embodiment, the identified at least one anatomical structure 210-240 is an acoustically hard anatomical structure 220 causing the at least one image artifact 250, 260 comprising a shadow 250 and/or a dark region 260. In a representative embodiment, the at least one beamformer parameter is automatically adjusted to avoid the acoustically hard anatomical structure 220. The automatic adjustment of the at least one beamformer parameter may comprise deactivating select transducer elements 106, 108 of an ultrasound probe 104 of the ultrasound system 100, adjusting beamforming weights, and/or adjusting beam angles. In various embodiments, the identified at least one anatomical structure 210-240 is an anatomy of interest defined by a selected protocol. In certain embodiments, the at least one beamformer parameter is automatically adjusted to increase an image contrast and/or an image sharpness at the location of the anatomy of interest. In an exemplary embodiment, the identified at least one anatomical structure 220 is associated with a pre-defined image artifact 250, 260. In a representative embodiment, the at least one beamformer parameter is automatically adjusted based on the pre-defined image artifact 250, 260 of the identified at least one anatomical structure 220. In certain embodiments, the method 300 may comprise automatically determining 306, by the at least one processor 132, 150, whether to automatically adjust the at least one beamformer parameter based on the identified at least one anatomical structure 210-240 and/or the at least one image artifact 250, 260.

Various embodiments provide a system 100 for providing ultrasound image enhancement by automatically adjusting beamformer parameters based on ultrasound image analysis. The system 100 may comprise an ultrasound system 100, at least one processor 132, 140, 150, 160, and a display system 134. The ultrasound system 100 may be configured to acquire an ultrasound image 202 and acquire an enhanced ultrasound image based on an automatically adjusted at least one beamformer parameter. The at least one processor 132, 140, 150, 160 may be configured to segment the ultrasound image 202 to identify at least one anatomical structure 210-240 and/or at least one image artifact 250, 260 in the ultrasound image 202. The at least one processor 132, 150 may be configured to detect a location of each of the identified at least one anatomical structure 210-240 and/or the at least one image artifact 250, 260. The at least one processor 132, 160 may be configured to automatically adjust the at least one beamformer parameter based on the detected location of one or more of the identified at least one anatomical structure 210-240 and/or the at least one image artifact 250, 260. The display system 134 may be configured to present the enhanced ultrasound image.

In a representative embodiment, the identified at least one anatomical structure 210-240 is an acoustically hard anatomical structure 220 causing the at least one image artifact 250, 260 comprising a shadow 250 and/or a dark region 260. In various embodiments, the at least one processor 132, 160 is configured to automatically adjust the at least one beamformer parameter to avoid the acoustically hard anatomical structure 220 by deactivating select transducer elements 106, 108 of an ultrasound probe 104 of the ultrasound system 100, adjusting beamforming weights, and/or adjusting beam angles. In certain embodiments, the identified at least one anatomical structure 210-240 is an anatomy of interest defined by a protocol selected via a user input device 130. In an exemplary embodiment, the at least one processor 132, 160 is configured to automatically adjust the at least one beamformer parameter to increase an image contrast and/or an image sharpness at the location of the anatomy of interest. In a representative embodiment, the identified at least one anatomical structure 220 is associated with a pre-defined image artifact 250, 260. The at least one processor 132, 160 may be configured to automatically adjust the at least one beamformer parameter based on the pre-defined image artifact 250, 260 of the identified at least one anatomical structure 220. In various embodiments, the at least one processor 132, 150 is configured to automatically determine whether to automatically adjust the at least one beamformer parameter based on the identified at least one anatomical structure 210-240 and/or the at least one image artifact 250, 260.

Certain embodiments provide a non-transitory computer readable medium having stored thereon, a computer program having at least one code section. The at least one code section is executable by a machine for causing the machine to perform steps 300. The steps 300 may comprise receiving 302 an ultrasound image 202. The steps 300 may comprise segmenting 304 the ultrasound image 202 to identify at least one anatomical structure 210-240 and/or at least one image artifact 250, 260 in the ultrasound image 202. The steps 300 may comprise detecting 308 a location of each of the identified at least one anatomical structure 210-240 and/or the at least one image artifact 250, 260. The steps 300 may comprise automatically adjusting 310 at least one beamformer parameter based on the detected location of one or more of the identified at least one anatomical structure 210-240 and/or the at least one image artifact 250, 260. The steps 300 may comprise receiving 302 an enhanced ultrasound image acquired 312 based on the automatically adjusted at least one beamformer parameter. The steps 300 may comprise presenting 302 the enhanced ultrasound image at a display system 134.

In various embodiments, the identified at least one anatomical structure 210-240 is an acoustically hard anatomical structure 220 causing the at least one image artifact 250, 260 comprising a shadow 250 and/or a dark region 260. The at least one beamformer parameter may be automatically adjusted to avoid the acoustically hard anatomical structure 220. The automatic adjustment of the at least one beamformer parameter may comprise deactivating select transducer elements 106, 108 of an ultrasound probe 104 of the ultrasound system 100, adjusting beamforming weights, and/or adjusting beam angles. In certain embodiments, the identified at least one anatomical structure 210-240 is an anatomy of interest defined by a selected protocol. The at least one beamformer parameter may be automatically adjusted to increase an image contrast and/or an image sharpness at the location of the anatomy of interest. In a representative embodiment, the identified at least one anatomical structure 220 is associated with a pre-defined image artifact 250, 260. The at least one beamformer parameter may be automatically adjusted based on the pre-defined image artifact 250, 260 of the identified at least one anatomical structure 220. In an exemplary embodiment, the steps 300 may comprise automatically determining 306 whether to automatically adjust the at least one beamformer parameter based on the identified at least one anatomical structure 210-240 and/or the at least one image artifact 250, 260.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing ultrasound image enhancement by automatically adjusting beamformer parameters based on ultrasound image analysis.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   acquiring, by an ultrasound system, an ultrasound image;
   automatically segmenting, by at least one processor, the ultrasound image to identify at least one obstructing anatomical structure and/or at least one image artifact in the ultrasound image;
   detecting, by the at least one processor, a location of each of the identified at least one obstructing anatomical structure and/or the at least one image artifact;
   automatically adjusting, by the at least one processor, at least one beamformer parameter based on the detected location of one or more of the identified at least one obstructing anatomical structure and/or the at least one image artifact, wherein the automatically adjusting the at least one beamformer parameter comprises deactivating select transducer elements of an ultrasound probe of the ultrasound system;
   acquiring, by the ultrasound system, an enhanced ultrasound image based on the automatically adjusted at least one beamformer parameter; and
   presenting, at a display system, the enhanced ultrasound image.

2. The method of claim 1, wherein the identified at least one obstructing anatomical structure is an acoustically hard anatomical structure causing the at least one image artifact comprising a shadow and/or a dark region.

3. The method of claim 2, wherein the select transducer elements of the ultrasound probe of the ultrasound system deactivated by the at least one processor are adjacent the acoustically hard anatomical structure.

4. The method of claim 1, wherein the identified at least one obstructing anatomical structure comprises ribs.

5. The method of claim 1, wherein the automatically adjusting, by the at least one processor, the at least one beamformer parameter further comprises adjusting beamforming weights.

6. The method of claim 1, wherein the identified at least one obstructing anatomical structure is associated with a pre-defined image artifact.

7. The method of claim 6, wherein the at least one beamformer parameter is automatically adjusted based on the pre-defined image artifact of the identified at least one obstructing anatomical structure.

8. The method of claim 1, wherein the automatically adjusting, by the at least one processor, the at least one beamformer parameter further comprises adjusting beam angles.

9. A system comprising:
  an ultrasound system configured to:
    acquire an ultrasound image, and
    acquire an enhanced ultrasound image based on an automatically adjusted at least one beamformer parameter;
  at least one processor configured to:
    automatically segment the ultrasound image to identify at least one obstructing anatomical structure and/or at least one image artifact in the ultrasound image;
    detect a location of each of the identified at least one obstructing anatomical structure and/or the at least one image artifact; and
    automatically adjust the at least one beamformer parameter based on the detected location of one or more of the identified at least one obstructing anatomical structure and/or the at least one image artifact, wherein the automatically adjust the at least one beamformer parameter comprises deactivating select transducer elements of an ultrasound probe of the ultrasound system; and
  a display system configured to present the enhanced ultrasound image.

10. The system of claim 9, wherein the identified at least one obstructing anatomical structure is an acoustically hard anatomical structure causing the at least one image artifact comprising a shadow and/or a dark region.

11. The system of claim 10, wherein the select transducer elements of the ultrasound probe of the ultrasound system deactivated by the at least one processor are adjacent the acoustically hard anatomical structure.

12. The system of claim 9, wherein the identified at least one obstructing anatomical structure comprises ribs.

13. The system of claim 9, wherein the automatically adjust the at least one beamformer parameter further comprises adjusting beamforming weights.

14. The system of claim 9, wherein:
  the identified at least one obstructing anatomical structure is associated with a pre-defined image artifact, and
  the at least one processor is configured to automatically adjust the at least one beamformer parameter based on the pre-defined image artifact of the identified at least one obstructing anatomical structure.

15. The system of claim 9, wherein the automatically adjust the at least one beamformer parameter further comprises adjusting beam angles.

16. A non-transitory computer readable medium having stored thereon, a computer program having at least one code section, the at least one code section being executable by a machine for causing the machine to perform steps comprising:
  receiving an ultrasound image;
  segmenting the ultrasound image to identify at least one obstructing anatomical structure and/or at least one image artifact in the ultrasound image;
  detecting a location of each of the identified at least one obstructing anatomical structure and/or the at least one image artifact;
  automatically adjusting at least one beamformer parameter based on the detected location of one or more of the identified at least one obstructing anatomical structure and/or the at least one image artifact, wherein the automatically adjusting the at least one beamformer parameter comprises deactivating select transducer elements of an ultrasound probe;
  receiving an enhanced ultrasound image acquired based on the automatically adjusted at least one beamformer parameter; and
  presenting the enhanced ultrasound image at a display system.

17. The non-transitory computer readable medium of claim 16, wherein:
  the identified at least one obstructing anatomical structure is an acoustically hard anatomical structure causing the at least one image artifact comprising a shadow and/or a dark region, and
  the deactivated select transducer elements of the ultrasound probe are adjacent the acoustically hard anatomical structure.

18. The non-transitory computer readable medium of claim 16, wherein the identified at least one obstructing anatomical structure comprises ribs.

19. The non-transitory computer readable medium of claim 16, wherein:
  the identified at least one obstructing anatomical structure is associated with a pre-defined image artifact, and
  the at least one beamformer parameter is automatically adjusted based on the pre-defined image artifact of the identified at least one obstructing anatomical structure.

20. The non-transitory computer readable medium of claim 16, wherein the automatically adjusting the at least one beamformer parameter further comprises adjusting beamforming weights and/or beam angles.

* * * * *